United States Patent
Kirwan et al.

(10) Patent No.: US 7,044,937 B1
(45) Date of Patent: May 16, 2006

(54) UNIVERSAL MODULAR SURGICAL APPLICATOR SYSTEMS

(75) Inventors: John M. Kirwan, Andover, MA (US); Dean M. Pichon, Arlington, MA (US); J. Jeffrey Kablik, Tyngsboro, MA (US); Stephen J. Herman, Andover, MA (US); Thomas S. Bromander, Andover, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/744,698

(22) PCT Filed: Jul. 27, 1999

(86) PCT No.: PCT/US99/16950

§ 371 (c)(1),
(2), (4) Date: May 14, 2001

(87) PCT Pub. No.: WO00/06216

PCT Pub. Date: Feb. 10, 2000

Related U.S. Application Data

(60) Provisional application No. 60/094,222, filed on Jul. 27, 1998.

(51) Int. Cl.
*A61M 5/178* (2006.01)
*A61M 5/00* (2006.01)
*A61B 17/00* (2006.01)

(52) U.S. Cl. .................. 604/264; 604/167.03; 604/524

(58) Field of Classification Search ................ 604/264, 604/13, 15, 96.01, 905, 195, 101.05, 284, 604/508, 523, 19, 48, 103.07, 194, 469.5, 604/101.01, 281, 164.03; 606/213.1, 318, 606/139

See application file for complete search history.

(56) References Cited

U.S. PATENT DOCUMENTS

| | | | |
|---|---|---|---|
| 4,911,704 A | 3/1990 | Dixon | |
| 5,149,330 A | 9/1992 | Brightbill | |
| 5,507,772 A | 4/1996 | Shutt et al. | |
| 5,575,815 A | 11/1996 | Slepian et al. | |
| 5,607,391 A | 3/1997 | Klinger et al. | |
| 5,662,712 A | 9/1997 | Pathak et al. | |
| 5,693,031 A * | 12/1997 | Ryan et al. ............ | 604/167.03 |
| 5,728,078 A | 3/1998 | Powers, Jr. | |
| 5,749,968 A | 5/1998 | Melanson et al. | |

(Continued)

FOREIGN PATENT DOCUMENTS

DE 195 18 801 A1 11/1996

(Continued)

Primary Examiner—Nicholas D. Lucchesi
Assistant Examiner—Roz Maiorino
(74) Attorney, Agent, or Firm—Thomas J. DesRosier; Richard D. Allison

(57) ABSTRACT

A modular system is described for construction of fluid applicators for open or endoscopic surgery from modular components. Lengths of tubing of various lengths, and devices to be carried by said tubing, are pre-fitted with standard adapters to mate with each other, thereby forming cannula sections and applicator sections. Interconnectors may also be provided, particularly for provision of articulation. The tubing is preferably rigid, but may also be either flexible or permanently bendable. A device can then be constructed by selection of a suitable set of tubing lengths, adapters and applicators. Devices customizable for particular uses can be created with minimal expense. The system is especially suitable for delivery of fluids to tissue in endoscopic or other minimally invasive surgical procedures. Delivery of fluids forming structure at a tissue site, especially as a hydrogel, is a preferred use of the devices.

22 Claims, 1 Drawing Sheet

U.S. PATENT DOCUMENTS

| | | |
|---|---|---|
| 5,752,972 A | 5/1998 | Hoogeboom |
| 5,759,169 A | 6/1998 | Marx |
| 5,766,157 A * | 6/1998 | Tilton, Jr. .................... 604/13 |
| 5,766,205 A | 6/1998 | Zvenyatsky et al. |
| 5,772,261 A | 6/1998 | Magram |
| 5,807,338 A | 9/1998 | Smith et al. |
| 5,810,721 A | 9/1998 | Mueller et al. |
| 5,817,072 A * | 10/1998 | Lampropoulos et al. .... 604/264 |
| 5,846,260 A | 12/1998 | Maahs |
| 5,865,817 A * | 2/1999 | Moenning et al. .......... 604/539 |
| 5,868,767 A | 2/1999 | Farley et al. |
| 5,876,344 A | 3/1999 | Baker et al. |
| 6,004,315 A | 12/1999 | Dumont |
| 6,010,495 A * | 1/2000 | Tilton, Jr. ..................... 606/1 |
| 6,146,373 A * | 11/2000 | Cragg et al. .................. 604/19 |
| 6,248,092 B1 * | 6/2001 | Miraki et al. ............... 604/905 |

FOREIGN PATENT DOCUMENTS

| | | |
|---|---|---|
| EP | 0 642 800 A1 | 3/1995 |
| WO | WO 90/01969 A1 | 3/1990 |
| WO | WO 91/12846 A1 | 9/1991 |
| WO | WO 94/21324 A1 | 9/1994 |
| WO | WO 95/09659 A1 | 4/1995 |
| WO | WO 96/00102 A1 | 1/1996 |
| WO | WO 96/19940 A1 | 7/1996 |
| WO | WO 96/29370 A2 | 9/1996 |
| WO | WO 97/36622 A1 | 10/1997 |
| WO | WO 98/22175 A1 | 5/1998 |
| WO | WO 00/15117 A1 | 3/2000 |

* cited by examiner

UNIVERSAL MODULAR SURGICAL APPLICATOR SYSTEMS

RELATED APPLICATIONS

This application claims the benefit under 35 U.S.C. §120 or 35 U.S.C. §365(c) of PCT International application PCT/US99/16950, designating the United States of America, and filed Jul. 27, 1999, of which this application is a national stage filing under 35 U.S.C. §371, published under PCT Article 21(2) in English.

Application number PCT/US99/16950 claims the benefit under 35 U.S.C. §119(e) of U.S. provisional application 60/094,222, filed Jul. 27, 1998.

FIELD OF THE INVENTION

The present invention relates generally to medical devices, and more particularly to a multi-component device for application of an agent to a body surface, which can be used surgically.

BACKGROUND OF THE INVENTION

Versatility and mobility in medical devices, particularly in medical devices to be used internally of a patient, are important, and can be especially important in minimally invasive surgical procedures. Minimally invasive surgical procedures are typically conducted through small ports, in contrast to the larger incisions typical of open surgery. Such procedures are called by a variety of adjectives, including endoscopic, laparoscopic, thoracoscopic, and the like. Endoscopic surgery will be used herein to describe these procedures.

Typical state of the art endoscopic procedures demand new families of instruments, and a variety of custom-designed instruments have been created for such procedures. Their common feature has been the ability to be passed through the cannula of a trocar, or other small opening (typically less than 1 cm. diameter) into the body, or through a natural orifice of the body. In contrast to the instruments of classical surgery, this requires a narrow diameter, and often the ability to manipulate the distal end of the device (the end within the body) from the proximal end (the end outside the body). Because endoscopic surgical procedures were initially perceived as extremely demanding, instruments were and are carefully optimized for each individual procedure. This custom optimization makes endoscopic instruments inherently expensive.

As the number of endoscopic procedures increases, there is a need to simplify the process of creation of suitable instruments, and to make their manufacture more efficient. This is especially important in the treatment of medical conditions with relatively small incidence, for example, those in which the annual incidence is a few thousands or tens of thousands.

In addition to endoscopic use, there is a similar need for specialized devices for various forms of open surgery which can be engineered and manufactured in an economical manner.

In many of these areas of surgery, there is an increasing use of structure-forming fluids, which may require custom variations in the design of the applicator. Examples of such custom uses include the local application of hydrogels, hydrogel precursors, and other structure-forming materials to form sealants, adhesives, pavings, barriers, tissue supports, tissue engineering substrates, and drug delivery depots.

Many medical devices with removable and interchangeable components are known. U.S. Pat. No. 5,507,772 (Shunt, et al.) discloses a surgical instrument including a removable tip assembly having an elongated support member including a proximal end configured to be coupled to a handle and a distal end for insertion into a patient's body. The surgical instrument includes a handle having a body portion formed to include an opening for receiving the proximal end of the tip and a locking mechanism for removably coupling the selected tip assembly to the handle.

U.S. Pat. No. 5,752,972 (Hoogeboom) discloses a modular surgical instrument which includes a handle, an end effector, and an elongate tubular sleeve extending between and opposing the end effector and the handle, a reciprocating actuator rod disposed within the sleeve. The disclosed arrangement allows an end effector to be easily removed from the handle and replaced with a different end effector, thus reducing costs associated with replacing one end effector and eliminating the need for providing each end effector with its own handle.

U.S. Pat. No. 5,766,157 (Tilton, Jr.) discloses a method and apparatus for laparoscopic insertion and application of a liquid, gel or like medicinal material that enables the laparoscopic surgeon to utilize various spray patterns to apply the desired material. The instrument consists of an elongated instrument body that can receive a selected flexible delivery tube having a distal end with a nozzle. The selected nozzle of the selected dispensing tube can be flexed to dispense with a desired spray pattern into any position of the patient's abdominal cavity.

U.S. Pat. No. 5,807,338 (Smith, et al.) discloses a modular trocar system which includes an obturator assembly, and a cannula assembly. A method of assembly is also provided and includes the steps of connecting a shield member, attaching a knife blade, and attaching a first housing section to a second housing section with a quick connect mechanism which includes first and second mating portions such that the first and second housing sections are movable from a spaced apart position to a connected position in a single motion.

U.S. Pat. No. 5,868,767 (Farley, et al.) discloses an intravascular universal catheter having interchangeable work elements and methods of use. Preferably, a lumen is configured to allow the work element to be completely withdrawn from the catheter body, so as to permit interchange of various work elements.

U.S. Pat. No. 5,876,344 (Baker, et al.) discloses a catheter assembly and method in which an imaging transducer is positioned proximally of a treatment device at the distal end of a catheter. The catheter, the treatment device, and the transducer are all constructed as individual modular units which can be assembled together as desired to form the assembly.

International Application WO 98/22175 (Sachdeva, et al.) discloses a modular balloon catheter with proximal and distal shaft which can be coupled by a connector made from a shape memory alloy. The proximal shaft of the catheter can be connected to the fluid supply source by either a conventional connector or a connector which is designed for and is made of a shape memory material.

While the above and other documents describe a variety of useful medical devices, modern demands for economy and speed have created a need for a better way of designing and making custom applicators. It is an object of the present invention to provide improved medical devices, especially for application of agents to body surfaces.

SUMMARY OF THE INVENTION

The present invention provides medical devices, kits, uses of devices and kits, and methods that meet the demands of specialized medical procedures, including surgical procedures, and particularly the delivery of specialized fluids internally of a patient. The invention provides standardized interconnectable modular components to create specialized devices, and meets the need for simplification, flexibility and efficiency in the creation and manufacture of specialized surgical instruments. The kits and devices of the invention are particularly adapted to control the delivery of structure-forming fluids and other agents to a sites in a patient. Kits can include a small set of types of components, which are connectable by a standard system of connectors.

In one aspect the invention provides a kit that can include cannula sections, sized and constructed for passage through a cannula, including a section of tubing pre-fitted with connectors; applicator sections for application of an agent to a body surface, exemplified by a brush, a spray nozzle, or other fluid-control device; optional adapter sections, which may facilitate a particular functionality, such as a limiting orifice for flow control, or means for articulation of the system.

An applicator can be constructed by providing an appropriate set of sterilized components and providing them as a medical device for a particular procedure, including a surgical procedure. Other components of a kit for the procedure may be provided in the same package, including fluids to be dispensed, containers for the fluids, and components for propelling fluids through the devices.

A surgical device is provided, as one aspect of the invention, and includes two or more modular units including at least a cannula section and an applicator section. The device is suitable for delivery of at least one fluid during surgery, and is capable of being provided in a sterilized condition.

The invention also provides a system for construction of a surgical device, wherein the device is assembled from two or more modular units including at least a cannula section and an applicator section, wherein the device is suitable for fluid delivery of at least one fluid during surgery and is capable of being provided in a sterilized condition.

The invention also provides a surgical system that includes a surgical device constructed and arranged for sterile passage through a cannula and able to deliver a therapeutic agent to a treatment site internally of a patient. The device includes at least one joint, at a portion of the device constructed to be passed through the cannula, that facilitates bending of the device.

In another aspect the invention provides a method for conducting endoscopic surgery. The method includes the use of a surgical device, wherein the device is assembled from two or more modular units including at least a cannula section and an applicator section, wherein the device is suitable for delivery of at least one fluid during surgery and is capable of being provided in a sterilized condition.

Another method of the invention in conducting surgery involves accessing a treatment site with a first device through a cannula, wherein the first device is a single component device or a multicomponent device, delivering a therapeutic agent to the treatment site via the first device, altering the first device to form a second device by carrying out at least one of adding a component to the first device, removing a component from the first device, and replacing a component of the first device with another component, and delivering a therapeutic agent to the treatment site via the second device.

Another aspect of the invention is a series of kits. One is a kit for performing a surgical procedure that includes a sterilizable device with two or more units removably attachable to each other, wherein the device is constructed and arranged for passage through a cannula and capable of delivering a therapeutic agent for application to a treatment site internally of a patient.

Another kit included in the invention includes a sterilizable device with two or more units removably attachable to each other at an articulating joint. The device is constructed and arranged for delivering a therapeutic agent for application to a treatment site internally of a patient.

Another kit for performing a surgical procedure according to the invention includes a device with two or more units including at least a cannula section and an applicator section removably attachable to each other. At least a portion of the device is capable of passage through a cannula for delivery of a therapeutic agent during surgery and the device is capable of being provided in a sterilized condition. The kit includes a third unit capable of being supplied in a sterilized condition and capable of being added to the device or interchanged with at least one unit of the device during said surgical procedure.

DETAILED DESCRIPTION OF THE INVENTION

Figure 1:
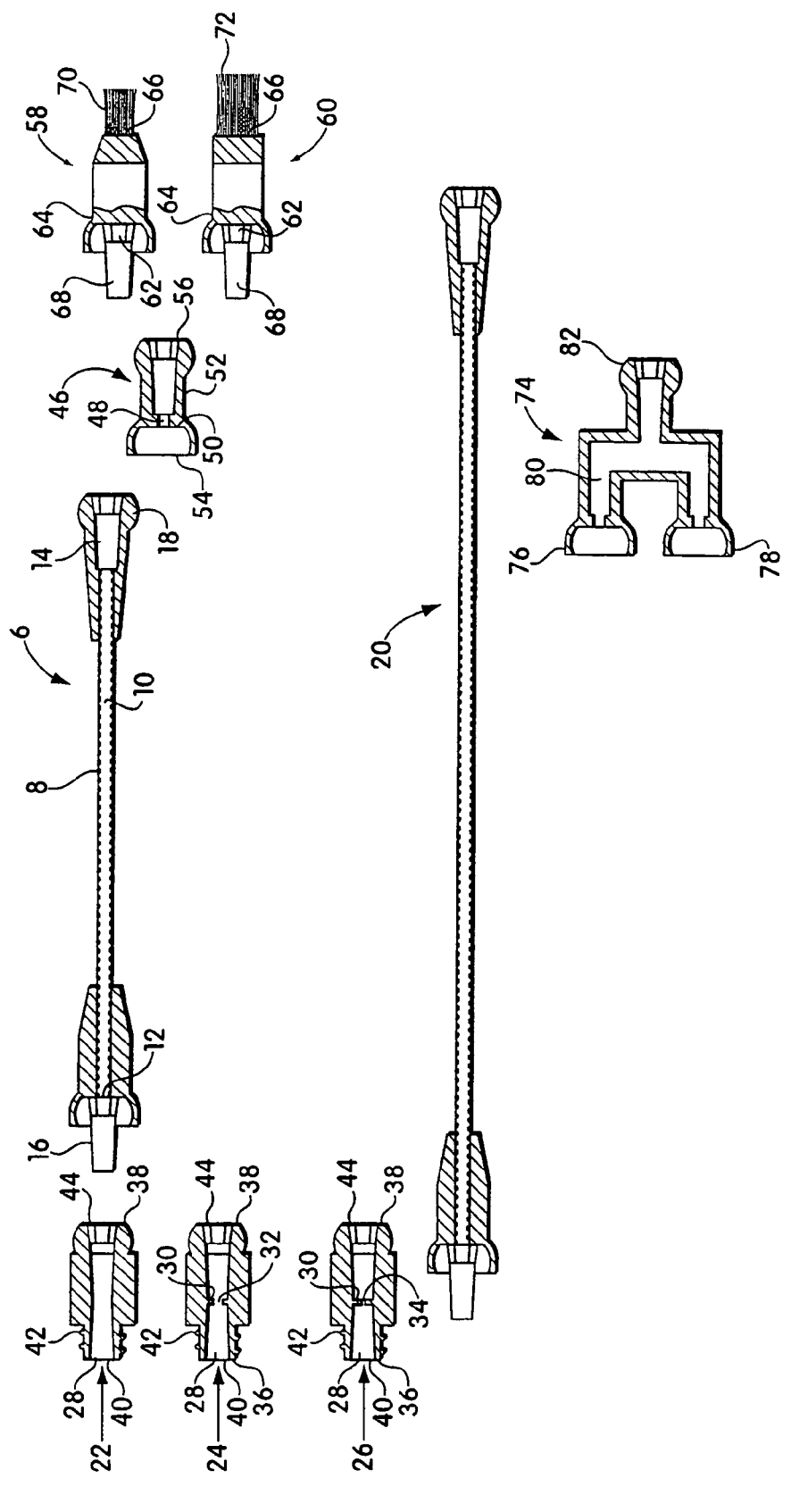
FIG. 1 is a schematic, cross-sectional illustration of some possible components of a multi-unit surgical kit in accordance with the invention.

FIG. 1 shows the components of one embodiment of a modular applicator kit of the invention. The term "modular" as used herein is used to describe standardized units or sections which are easily attached and detached from each other, some of which can be interchanged with one another to form a variety of configurations. The kit includes a variety of units removably attachable to one another that can be mixed and matched to form a variety of devices for application of an agent to a body surface.

A modular applicator kit of the invention as illustrated in FIG. 1 includes at least two components, a cannula section and an applicator section. More typically, a modular applicator will further comprise at least one adapter section, which will typically perform a particular function in the system. In FIG. 1 a cannula section 6 includes tube 8 defining a lumen 10 passing between a proximal end 12 and a distal end 14 of the section. A male Luer connector 16 is affixed to proximal end 12 and is in fluid communication with lumen 10. A male half of a ball and socket joint 18 is affixed to distal end 14 and is in fluid communication with lumen 10. A second cannula section 20 can be used with, or instead of cannula section 6, and differs from cannula section 8 in that it is longer. Other cannula sections can be used that are different from those illustrated, including those of different length, shape, internal and external diameter, etc. Some may have a particular non-linear fluid pathway, including joints at which they can be bent, rotated, and/or articulated. The term "articulation" as used herein means a relationship between a first and a second component or first and second portions of a single component where the axis of the first can move in three dimensions relative to the axis of the second, i.e. the type of movement allowed by a ball-and-socket joint. Articulation can be partial, or complete. That is, the first axis can rotate in arcuate relationship to the second through a portion of a circle, e.g. 90°, 180°, or 270°, or as in a ball-and-socket joint rotation can be throughout an entire circle, i.e. 360°. This movement can be through a continuum of circles of differing radii, that is, as in a ball-and-socket joint. "Bend", herein means a situation where the first moves in two dimensions relative to the second; movement exhibited by the human elbow.

"Cannula section", as used herein, is meant to define a portion of a device that is constructed to have a lumen which can serve as a passageway for fluids or other components. In addition, a cannula section will often be constructed so that it is suitable for passage through the lumen of a larger cannula which gives access to a location within a patient. Cannula sections can be used without a cannula, and it is to be understood that any arrangement of the invention can be used without a cannula, i.e. in a procedure other than an endoscopic procedure. Minimally invasive surgical procedures are typically conducted through small ports, in contrast to the larger open incisions typical of previous medical practice. Such procedures are called by a variety of adjectives, including endoscopic, laparoscopic, thoracoscopic, and the like. The term "endoscopic" will be used herein to refer to all procedures of this type.

As illustrated, the kit includes adapter sections 22, 24 and 26, each having a hollow interior, or fluid pathway 28 between a proximal end 38. Adapter section 24 further includes a baffle 30, with an orifice 32, inside hollow interior 28. Adapter section 26 further includes a baffle 30 with an orifice 34 inside hollow interior 28. Orifice 34 is of a different size than orifice 32, orifice 34 being smaller than orifice 32. Adapter sections 22, 24, and 26 thus provide different restrictions on fluid flow through their fluid pathways, allowing different rates of fluid flow therethrough, and can be selected for used in a device constructed from the kit to control fluid flow as desired.

Adapter sections 22, 24 and 26 each have a proximal end 36 comprising male connector 40 with threads 42 adapted to be received by a corresponding connector, not shown, and an opening in fluid communication with hollow interior 28. Adapter sections 22, 24, and 26 each have a distal end 38 comprising a male half of a ball and socket joint 44 including an opening in fluid communication with hollow interior 28. The distal end 38 of each adapter section is reversibly connectable to the proximal end 12 of the cannula section.

An adapter 46 is provided which has a hollow interior 48 between a proximal end 50 and a distal end 52 thereof, and is designed to serve as an interconnector between an applicator (described below) and the cannula, and also can provide articulation therebetween. Proximal end 50 of adapter 46 includes a female half of a ball and socket joint 54 including an opening in fluid communication with hollow interior 48, and is removably attachable to distal end 14 of the cannula section. Distal end 52 of adapter 46 includes a female Luer taper 56 including an opening in fluid communication with hollow interior 48, and is removably attachable to the proximal end of an applicator, described below.

The kit includes applicators 58 and 60, each or which have a hollow interior 62 between a proximal end 64 and a distal end 66 thereof. Proximal end 64 of each applicator section 58 and 60 includes a male Luer connector 68 including an opening in fluid communication with hollow interior 62. Distal end of 66 applicator section 58 carries a brush 70 for controlled application of an agent to a body surface. Distal end of applicator section 60 includes a brush 72. Brush 70 differs from brush 72 in size, brush 70 being the smaller of the two. A distal section similar to section 58 or 60 can provide other functions, such as a spray, nozzle, a spreading pad, a roller, a paddle, a molding member and an expandable member.

It is a feature of the kit illustrated in FIG. 1 that a variety of devices can be constructed for a variety of purposes and medical applications including surface treatment, open surgery of an internal surgical site, endoscopic surgery and surgery conducted through a natural body orifice. For example, for rapid flow of agent through the device and large-scale application of agent to a body surface relatively far from the proximal end of the device, adapter section 22 can be connected to cannula section 20, which is connected to adapter 46, which is connected to applicator section 60. For slower flow of agent (at similar applied agent pressure) through the device and smaller-scale application of agent to a body surface closer to the proximal end of the device, adapter section 26 can be connected to cannula section 6, which is connected to adapter 46, which is connected to applicator section 58. Any combination can be assembled, where connections are matable. It is to be understood that although different mating connections are illustrated, all connections could be the same, e.g. all could be ball-and-socket connections such as the connection between distal end 14 of the cannula section and the proximal end of adapter 46. This arrangement allows for essentially unlimited versatility in selection of components when constructing a device. In such an arrangement both cannula sections 6 and 20 could be used, optionally separated by an adapter section 22–26 for fluid flow control.

It will be appreciated that the various connections illustrated in FIG. 1 and described above allow differing degrees of relative movement between components of the kit. For example, connection of any of adapter sections 22–26, as illustrated, to either of the cannula sections 6 or 20 creates a coupling where each component can rotate about the axis of either, but hinged bending and articulation is prevented. Although not shown, a joint can be made that is essentially rigid, i.e. any movement, including axial rotation, is prevented by providing a notch-in-groove connection integral with the connection as shown, or other known arrangement. It can be seen that a ball-and-socket joint formed by connection of cannula section 6 or 20 to adapter 46 allows bending of adapter 46 (and, hence, brush 58 or 60 where connected to the adapter) relative to the cannula section, even articulation. This allows flexibility in the system, so that the brush can be bent, and rotated, with respect to the cannula. Accordingly, any connection between any unit may be made rigid, may be rotational about either component, or may allow articulation of one unit with respect to the other.

The modular applicator system is designed to connect to a proximal fluid source (not illustrated), which can connect to the left end of the application system as illustrated (proximal end). Examples of such a fluid source include a filled syringe, a hose connected to a reservoir, or a specialized pump or metering device.

The importance of a modular system for creation of surgical instruments can be appreciated by considering the large variety of devices which can be assembled from just the nine different components shown in FIG. 1. A minimal device would contain one of the two cannula sections (assumed to be of different length and/or shape) and one of the two applicator sections (4 options), thereby creating four basic configurations. Each of the four basic configurations could contain one of the three orifice-carrying adapter sections, and/or one of the illustrated articulating adapter sections. Note that if the articulating unit adapter is omitted, the applicator (brush) can be fitted to a Luer taper in the right end of the cannula. This allows many different systems to be assembled from a basic inventory of nine components. More complex systems, containing additional components (for example, an additional cannula section connected through another articulating adapter section) are possible. The more complex systems may include two elements, preferably 3, 4, 5 or 6 components.

System Elements

1. Cannula Sections ("Cannulas")

In the preferred embodiment, these are lengths of hollow tubing, to which connectors have been affixed. The tubing may be of any consistency or material which is suitable for endoscopic or other use described above. A preferred material is stainless steel tubing, for example hypodermic needle tubing stock. For use as a disposable device, less expensive materials may be suitable, including coated metal, rigid plastic, and flexible plastic. For insertion through a narrow trocar cannula or other small opening, the entire applicator assembly must be both small enough and sufficiently rigid to pass through the opening and still allow manipulation of the proximal applicator section from the distal end of the apparatus.

The connectors, both in cannula sections and in modules of the invention, may operate by any system of connections suitable for medical use. These include friction-fit joints, such as tapered joints; snap-fit connections, including ball-and-socket joints; screw connections; clamped or pressure joints; bayonet-lock joints; and glued joints. The simpler forms, such as tapered friction-fit joints and snap-fit joints, are preferred.

The connections should be adequately resistant to agents, or materials to be applied for at least one-time use. The assembly should maintain its integrity in use. Depending on the pressures and forces to be applied, this may be as simple as a tapered friction-fit, such as a Luer taper or other taper, or a simple snap-fit ball-and-socket joint ("ball joint"). Combinations of connection types are possible, as is illustrated in the Figure, where all joints have a snap-fit ball joint capability, and all male ball halves also have female friction fit capability. Some female ball sections also carry male taper fit connectors, which provides rigidity at the joint.

For higher pressure, the use of a locking mechanism, such as a bayonet lock, for example a "Luer-Lock" type of connector, or of a snap joint as shown, is preferred. Friction-type connectors may also be glued together, where disassembly is not required or not contemplated. Snap-fit ball joints may be further secured by known means, such as retaining rings or clips, and clips and other restraining means may be used to secure friction joints. Threaded connections may be used, in particular in combination with ferrules and gaskets.

In all cases, the finished cannula section should be capable of being sterilized, preferably by one or more, more preferably by two or more, of the principal systems for sterilization in commercial use. These include gamma ray or electron beam sterilization; ethylene oxide sterilization; plasma treatment e.g. with peroxide; and autoclaving. The kits and devices are made of a material that can withstand one or more of the sterilization techniques. In one embodiment of the invention, the kits and devices are provided in a sterilized condition.

Although illustrated as having a single flow path, a system of the invention may have multiple fluid flow paths, which may also diverge or merge in passing through the device. Moreover, a pair of devices, consisting of flow orifices, cannula sections and adapter sections, can be linked together by a common fluid mixing element 74. Mixing element 74 includes two proximal female halves of a ball and socket joint 76 and 78, each including an opening in fluid communication with hollow interior 80, and each removably attachable to distal end 14, of a first cannula section and a second cannula section, respectively. Mixing element 74 also has a distal female Luer taper 82 including an opening in fluid communication with hollow interior 80, and is removably attachable to the proximal end of an applicator, as previously described. Mixing element 74 therefore, has the capability of bending and articulating where jointed to the cannula and also, rotating where jointed to the applicator.

2. Applicator Sections

The particular form of the applicator section ("applicator") will depend on the fluid to be applied and the way in which it is to be distributed on the tissue. Any known fluid-dispensing means may be used in the invention, provided that it is compatible with the fluid to be used; configured so that the operator (typically a physician) can properly apply the fluid to the appropriate site in the patient; optionally capable of fitting through a trocar cannula or similar opening; and sterilizable as described above. Examples of types of applicators are: open tubes, straight-cut or beveled, for dripping or other direct dispensation; brushes, with an opening in the proximal end for fluid to enter the brush and/or flow through the brush to the tissue surface; rollers, paddles, pads, and similar devices, optionally with a proximal opening for fluid, to smooth or re-arrange a fluid on a surface, especially a viscous fluid; nozzles for producing divided streams of fluid, or sprays; molding members, into which fluid may be injected so that it forms a definite shape after injection into the body, and after curing if desired; and expandable applicators which receive fluid and then can be expanded to apply fluid to a surface. At least one of these applicator types, or a functional equivalent, will normally be present in the devices of the invention 3. Adapter Sections Adapter sections ("adapters") may provide any of a variety of functions. In the simplest form, they simply connect two other sections which have different styles of connection. They may provide an articulation function; an example is illustrated in FIG. 1. A variety of other types may be needed, such as male—male or female—female adapters. Adapters may also perform a flow-related function. In FIG. 1, the leftmost adapter is designed to have a limiting orifice, so that the pressure drop in the distal (right) apparatus is limited at a particular flow rate. This is important in a pressure-fit system. Other functions in an adapter section can include mixing of fluid streams, ratioing of fluid streams, and valving functions. The latter can include one-way valves, and pressure-release valves, if required for the particular fluid applications.

Other System Features

The basic system may optionally have any of a number of ancillary features to enhance its utility or safety. These include radio-opacity, for visibility under fluoroscopy, or to assist in retrieval if required; color-coding to guide selection of correct sections or of correct entire devices; controlled flexibility, via ball joints, flexible or bendable tubing, or other means; non-magnetic for use in MRI systems; intra-operatively removable applicators, for complex applications or in case of plugging; and provision for passage of optical fibers or other emitters of radiation, or sensors of conditions at the application site, through the lumen of the device.

Methods of Module Manufacture

Modules may be made by any convenient method. Preferred methods will be conducive to efficiency and cost-effectiveness, but the presence of more expensively-manufactured components in an assembled surgical device, especially in a prototype or short run device, is compatible with the objectives of the invention.

1. Machining. Initial prototypes of many system components, especially adapters and applicators, will be made by machining, either from partially precast blanks or from raw materials such as plastic or metal.

2. Injection or pressure molding. At higher volumes, most system components will be made by injection molding to final tolerance. In some cases, such as orifice-carrying adapters, the orifice may be drilled into a blank septum, since the drilling operation is simple.

3. Combination methods. The cannula section modules preferably carry connectors on a length of tubing. The preferred method of making such cannulae is to render the tubing ends capable of retaining a molded connector, and to provide a premolded connector part for each end. In a preferred embodiment for higher volume systems, a mold for forming the connector is provided, and the tubing end is inserted into the molding apparatus. A shut-off block may be provided in the mold to prevent flow of the molded material, typically a thermoplastic or thermosetting plastic, into the lumen of the cannula. In such a system, the tubing near the end is typically modified to retainingly engage the connector on the tubing. This may be provided by holes or slots in the tubing; by roughening or knurling of the tubing; by provision of a ferrule swaged to the tube; or by other conventional means known in the art.

Alternatively, and especially in prototyping, a preformed connector is slid or pressed onto a tube end, and the end of the tubing is then flared to retain the connector. This method typically requires a gasket for fluid retention.

The preformed cannulas can be formed into standardized bent shapes if required. This can be done with a mandrel or other known tube-bending device. The bending may be done before assembly of the connectors with the tubing, but is preferably performed later. Cannulas can be provided in a variety of stock lengths, such as integral numbers of centimeters or inches.

Fluids to be Delivered

Any fluid may be delivered by the surgical devices of the invention. Preferred fluids are those which require a significant degree of control on application to the site, such as fluids containing drugs, or air flows used to clean or compress specific tissue areas (as opposed to, for example, irrigating fluids). Fluids requiring a higher degree of control in their site of application are especially preferred. These include materials which form structure at the site of application. Structures include sealants, adhesives, pavings, coatings, barriers, drug delivery depots, and tissue engineering matrices. Fluids forming such structures are typically one or more of film-forming polymeric systems and gel-forming organic systems. These may be comprised of a fluid small-molecule pre-polymeric material, or preferably a fluid polymer-containing material, which forms structure at the site by at least one of precipitation, coacervation, gelation, spontaneous reaction, or reaction stimulated by application of energy. More than one material may be applied through the device, or through multiple devices, to cause such structure formation. Component 74 of FIG. 1 allows simple mixing of two-component materials essentially immediately prior to application, and application of the resulting mixture to a body surface, optionally through a bending or articulating joint. The materials may be of natural origin, but are preferably synthetic. Numerous suitable materials are described in the art. Hydrogel-forming materials are preferred. Typical agents to be applied include therapeutic agents, a term used herein to define any fluid which is of benefit to a patient, and preferably are at least one or a combination of drugs, barrier forming fluids, or structure forming fluids. One embodiment of the invention delivers hydrogels and/or hydrogel precursors to a treatment site of a patient. Agents can be selected among those described in U.S. Pat. Nos. 5,410,016; 5,573,934; 5,800,373; 5,844,016; 5,900,245; 5,410,016; 5,573,934; 4,938,763; 5,100,992; 4,826,945; 4,741,872; 5,160,745; 4,511,478; 5,198,507; or 5,219,564 or in co-pending U.S. application Ser. Nos. 08/973,077 and 08/944,739 as well as in International Patent Publication Nos. WO 96/29370, WO 98/2243 and WO 99/07417. The disclosures of the above-identified documents are incorporated by reference as part of the disclosure herein.

What is claimed is:

1. A method of conducting surgery, the method comprising:
   accessing a treatment site with a first device through a cannula, wherein the first device is a multicomponent device comprising a first unit and a second unit, the first and second units together defining a first articulating joint such that the two units which define the first articulating joint can move in three dimensions relative to each other;
   delivering a therapeutic agent to the treatment site via the first device;
   altering the first device to form a second device by replacing the first unit of the first device with a third unit to form the second device, such that the second and third units together define a second articulating joint wherein the two units which define the second articulating joint can move in three dimensions relative to each other; and
   delivering a therapeutic agent to the treatment site via the second device.

2. A The method of claim 1, wherein the first device comprises two or more modular units, at least one of which is capable of being interchanged during surgery, including at least a cannula section and an applicator section, wherein the first device is capable of being provided in a sterilized condition, and wherein the first device further comprises at least one adaptor section.

3. A method according to claim 1, wherein the first articulating joint is a snap-fit ball and socket joint.

4. A device method according to claim 1, wherein the first articulating joint comprises both a taper fit connection and a snap-fit ball and socket connection.

5. A method according to claim 1, wherein the first device further comprises at least one of a valve and a limiting orifice.

6. A method according to claim 1, in which the therapeutic agent is contained by a fluid which forms at least one structure at the application site.

7. A method according to claim 6, in which said structure includes sealings, adhesives, pavings, coatings, barriers, drug delivery depots, and tissue engineering matrices.

8. A method according to claim 6, in which said fluid forms the structure at the site by at least one of precipitation, coacervation, gelation, spontaneous reaction, or reaction stimulated by application of energy.

9. A method according to claim 1, wherein said first device is assembled from modules wherein at least one module comprises a molded part.

10. A method according to claim 9, wherein the at least one module has the attribute of at least one of radio-opacity; color-coding; controlled flexibility; lack of magnetic responsiveness; intraoperative removability; and passability therethrough of optical fibers or sensors.

11. The method of claim 2, wherein said applicator section is at least one of an open tube; a brush; a roller; a pad; a paddle; a nozzle; a molding member; and an expandable member.

12. A method according to claim 1, wherein the first device is sterilizable by at least one of gamma irradiation, electron-beam irradiation, ethylene oxide sterilization, plasma treatment, and autoclaving.

13. A method according to claim 1, wherein the therapeutic agent is selected for treatment of a predetermined medical condition.

14. The method according to claim 1, wherein at least one of the units comprises a molded part.

15. The method according to claim 1, wherein at least one of the units has the attribute of at least one of radio-opacity; color-coding; controlled flexibility; lack of magnetic responsiveness; intraoperative removability; and passability therethrough of optical fibers or sensors.

16. The method according to claim 2, wherein the applicator section is a brush.

17. The method according to claim 1, wherein at least two or more of the units slidably connect to one another in fluid communication with one another to form the articulated joint.

18. The method according to claim 1, wherein the first articulated joint further comprises a first slidably connectable piece and a second slidably connectable piece.

19. The method according to claim 18, wherein the first slidably connectable piece is affixed to the cannula section and the second slidably connectable piece is affixed to the applicator section.

20. A method as in claim 1, wherein the first articulating joint facilitates at least 90° rotational movement of the first unit relative to the second unit.

21. A method as in claim 1, wherein the first articulating joint facilitates at least 180° rotational movement of the first unit relative to the second unit.

22. A method as in claim 1, wherein the first articulating joint facilitates 360° rotational movement of the first unit relative to the second unit.

* * * * *